United States Patent [19]
Fehlau et al.

[11] 4,210,153
[45] Jul. 1, 1980

[54] MEDICAL DIAGNOSTIC DEVICE FOR DETERMINING BLEEDING TIMES AND BEHAVIOR OF BLEEDINGS FROM A STANDARDIZED WOUND

[75] Inventors: Robert Fehlau; Peter Schlussel; Matthias Schneider, all of Freiburg, Fed. Rep. of Germany

[73] Assignee: Hellige GmbH, Freiburg im Breisgau, Fed. Rep. of Germany

[21] Appl. No.: 11,261

[22] Filed: Feb. 12, 1979

[30] Foreign Application Priority Data

Feb. 28, 1978 [DE] Fed. Rep. of Germany ....... 2808473

[51] Int. Cl.$^2$ ............................................. A61B 5/00
[52] U.S. Cl. .................................................. 128/637
[58] Field of Search ....................... 128/637, 633, 638

[56] References Cited
FOREIGN PATENT DOCUMENTS 568062 10/1975 Switzerland ............................ 128/637

OTHER PUBLICATIONS

Sutor, A. H., et al., *Amer. Journ. of Clinical Pathology*, vol. 55, (1971), pp. 541–550.

*Primary Examiner*—Kyle L. Howell
*Attorney, Agent, or Firm*—W. R. Thiel; N. E. Brunell; A. L. Levine

[57] ABSTRACT

Disclosed herein is a medical diagnostic device for determining bleeding times and behavior of bleedings from a standardized wound, (hemmorrhagometry), wherein a flow of a rinsing liquid past the wound is established, thereby to cause the rinsing liquid to contact the wound. A photometric instrument or equivalent is provided for determining a characteristic of the rinsing liquid which is representative of the proportion of blood contained in the rinsing liquid having contacted the wound. The device of the invention is designed such that it permits controlling the temperature of the rinsing liquid and consequently of the bleeding location and of its surrounding area, in order to keep them on a preselected temperature. Temperature control is suitably achieved by means of a thermo-electric device which includes a first heat exchanger for receiving the flow of the rinsing liquid therethrough, a second heat exchanger for receiving the flow of a second liquid therethrough, a Peltier element in thermal contact with the first and second heat exchangers, and circuitry operable as a closed-loop servo-system for controlling energization of the Peltier element as a function of the temperature of the rinsing liquid, thereby to maintain the rinsing liquid temperature at a substantially constant level.

10 Claims, 2 Drawing Figures

MEDICAL DIAGNOSTIC DEVICE FOR DETERMINING BLEEDING TIMES AND BEHAVIOR OF BLEEDINGS FROM A STANDARDIZED WOUND

FIELD OF THE INVENTION

This invention relates to medical diagnostic devices for determining bleeding times and behavior of bleedings from a standardized wound (hemorrhagometry).

DESCRIPTIONS OF THE PRIOR ART

Medical diagnostic apparatus or equipment of the type referred to above is known to be very useful in connection with the medical diagnostic procedure called hemorrhagometry, by which properties of the blood are observed by measuring the bleeding time, the bleeding intensity and the blood loss from a standardized skin wound, thereby to determine the blood's capability to coagulate. The principle of the diagnostic method of hemorrhagometry is described in the publication "Bleeding from Standardized Skin Punctures" by A.H. SUTOR; E.J. BOWIE; J.H. THOMPSON; JR.; P. DIDISHEIM; B.F. MERTENS and Ch.A. OWEN, JR.; Amer. Journal of Clinical Pathology, Vol. 55: (1971), p. 541 through 550.

SUMMARY OF THE INVENTION

A medical diagnostic device is described for determining bleeding times and behavior of bleedings from a standardized wound, wherein the flow of a rinsing liquid is established to conduct the rinsing liquid past the wound, so that it comes into contact with the wound, and wherein the rinsing liquid having contacted the wound is conveyed into equipment which determines a characteristic of the rinsing liquid which is representative of the blood proportion contained therein, with the temperature of the rinsing liquid being kept at a preselected level, suitably by the use of a thermo-electric device, in order to enable measurements of bleeding times and the behavior of bleeding from a standardized wound, which is cooled or heated by the rinsing liquid. Besides measurements at room temperatures, for example at 25° C., for the so-called tolerance test, the liquid may be cooled to 16° C. or 17° C., whereas for the measurement of heat-lysis time the temperature may be raised to from 41° C. to 43.5° C., where a sealed wound begins again to bleed within a minute.

The concept of a standardized wound and an instrument for creating such wounds are discussed and disclosed in co-pending Application Ser. No. 828,711, filed Aug. 20, 1977, and assigned to the same assignee. Further, reference is made to the review "Quantitative Bleeding Time (Hemorrhagometry)", published by A.H. SUTOR; E.J. BOWIE and C.A. OWEN JR. in Myo-Clin, Proc., April 1977, Vol. 52: p. 238 through 240.

In describing a preferred embodiment of the invention, a thermo-electric device is disclosed which is particularly designed and useful as that component of the equipment of the invention which maintains the temperature of the rinsing liquid at a substantially constant level. Such thermoelectric device includes two heat exchangers of which a first one receives the flow of the rinsing liquid, while the second heat exchanger receives the flow of another, so-called auxiliary liquid which may suitably be maintained at a substantially constant temperature, there being a Peltier element mounted between the heat exchangers and thus in thermal contact with each of the two heat exchangers, and wherein the assembly thus described includes an arrangement for controlling energization of the Peltier element as a function of the temperature of the rinsing liquid.

In accordance with details of the embodiment illustrated herein, as described further below in connection with the drawings, the thermo-electric device for use in the medical diagnostic device of the invention includes, as one of its more essential components, the Peltier element and the two heat exchangers which are in close heat-transferring relationship to the electrodes of the Peltier element. The electrodes, during operation, perform as the heat sink and the heat source of the Peltier element. One of the heat exchangers receivers the flow of the liquid whose temperature is to be thermostatically controlled, which is the rinsing liquid, while the other receives the flow of the auxiliary liquid which accomplishes a precooling or preheating effect, maintaining the temperature of the adjacent electrode of the Peltier element at a temperature at least in vicinity of the desired temperature. The Peltier element operates to accomplish fine adjustment of the temperature of the rinsing liquid in the first heat exchanger. Furthermore, the apparatus includes a temperature sensor for sensing the temperature of the liquid which is to be thermostatically controlled, and the output signal from the temperature sensor controls the energization of current for the Peltier element via an associated circuit, including a controller.

BRIEF DESCRIPTION OF THE DRAWINGS

The invention will become better understood from the following detailed description of one presently preferred embodiment thereof, when taken in conjunction with the drawings, wherein.

DETAILED DESCRIPTION OF THE PRESENTLY PREFERRED EMBODIMENT

Figure 1:
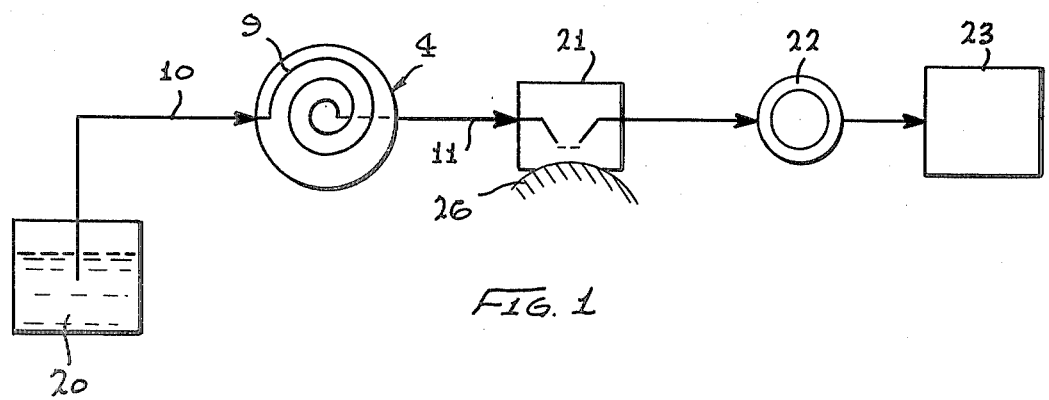
FIG. 1 is a schematic illustration of a medical diagnostic device in accordance with the invention.

When investigating the bleeding times and behavior of bleedings from a standardized wound it was found that the temperature of the wound has an important influence upon the various observable occurrences. It is actually possible to significantly widen the scope of diagnostic information by establishing well-determined temperatures of the wound which deviate from the normal body temperature level.

The invention is thus based upon the principle that, for the purpose of such diagnosis, in a typical embodiment, use can be made of a rinsing liquid which is conducted through a flow-through cuvette applied to the wound, and whose temperature is adjustable to a predetermined level. Then, it becomes possible to conduct tests at different temperature levels. For the purpose of hemorrhagometry under normal temperature conditions, the desired temperature level may be 25° C. For the hemorrhagometry under the influence of cold on the wound (cold tolerance test) the desired temperature level may be 16° C. or 17° C., and for the hemorrhagometry under the influence of heat applied to the wound (measurement of the heat-lysis time), the desired temperature level of the rinsing liquid may be raised to a constant value between 41° C. and 43.5° C. The device of the illustrated embodiment of the invention permits thermostatically controlling the temperature of such rinsing liquid, so that it can be adjusted to be maintained at a predetermined temperature.

The invention additionally involves the result of a search for a solution of the problem of maintaining accurately at a predetermined temperature even a small quantity of a liquid which flows through a pipe or hose, which temperature can substantially deviate from the normal body temperature or from ambient temperature. Such apparatus should desirably be of relatively light weight, space-saving construction, and it should be easily cleaned and sterilized, particularly for the described use. Also, the temperature control should be capable of implementation with small technological investments.

In the presently preferred embodiment of the invention, described and illustrated herein, the medical diagnostic device may include a reservoir from which the rinsing liquid is pumped through the thermo-electric device, through a flow-through cuvette which can be positioned adjacent to the wound and to a device which determines a characteristic of the rinsing liquid, which latter, in practice, is preferably a photometric arrangement comprising a light-transmissive container for the rinsing liquid, a light source, a photocell which receives the light emitted from the source and passed through the container and a photometric arrangement for reading out, monitoring and/or recording the light intensity applied to the photocell. Altogether, photometric equipment and instruments of this type are well known in the art and need not be described in detail.

As will be seen from the detailed description further below, controlled energization of the Peltier element can be performed by the use of a temperature sensing probe and a controller which, together with a source of electrical power, operate as a closed-loop servo-system to maintain the rinsing liquid at a constant temperature level. Specifically, the controller permits adjustment to obtain a constant temperature level of the rinsing liquid by energizing the Peltier element whenever the temperature represented by the output signal from the temperature sensor deviates from a selected desired value. It will be seen that, considering that a Peltier element, when energized, causes transfer of heat energy from one of its electrodes to the other electrode, the auxiliary liquid in the second heat exchanger, when maintained at a constant temperature, will operate to maintain the entire assembly in the vicinity of the desired temperature, i.e. preheat or precool it. Thus, the adjacent electrode can be stated to be "clamped" to the temperature of the auxiliary liquid which then will be the basis for the function of the Peltier element, inasmuch as the Peltier element will then merely have to perform the function of fine adjustment to bring the temperature of the rinsing fluid in the first heat exchanger substantially to the level to which the controller has been set by an operator.

Referring now to the drawings, FIG. 1 is a schematic illustration of a medical diagnostic device constructed in accordance with the invention. The rinsing fluid, initially contained in receptacle 20, is conveyed from the receptacle through a pipeline 10, or other suitable conduit, into a thermo-electric device which operates to maintain the temperature of the rinsing liquid constant. In FIG. 1, the thermo-electric device is schematically indicated by showing a heat exchanger 4 with a spiraling channel 9 for the rinsing liquid, with the details of the thermo-electric device being explained further below in connection with a description of FIG. 2.

The rinsing liquid leaving the heat exchanger 4 is conveyed through a pipeline 11 into a flow-through cuvette 21, which is schematically illustrated as being applied to that portion of a human body 26 where the standardized wound has been made. The rinsing liquid, after having contacted the wound, is conveyed by a pump 22 into a photometric instrument 23, which is only schematically illustrated in FIG. 1, as instruments of this type are well known in the art.

The photometric instrument 23 may be of any conventional type including a light-transmittive container, a source of light, a photocell which receives light from the source after it has passed through the light-transmissive container and circuitry for monitoring, and suitably also recording, the output from the photocell, which then is indicative of the blood contents in the rinsing fluid.

Figure 2:
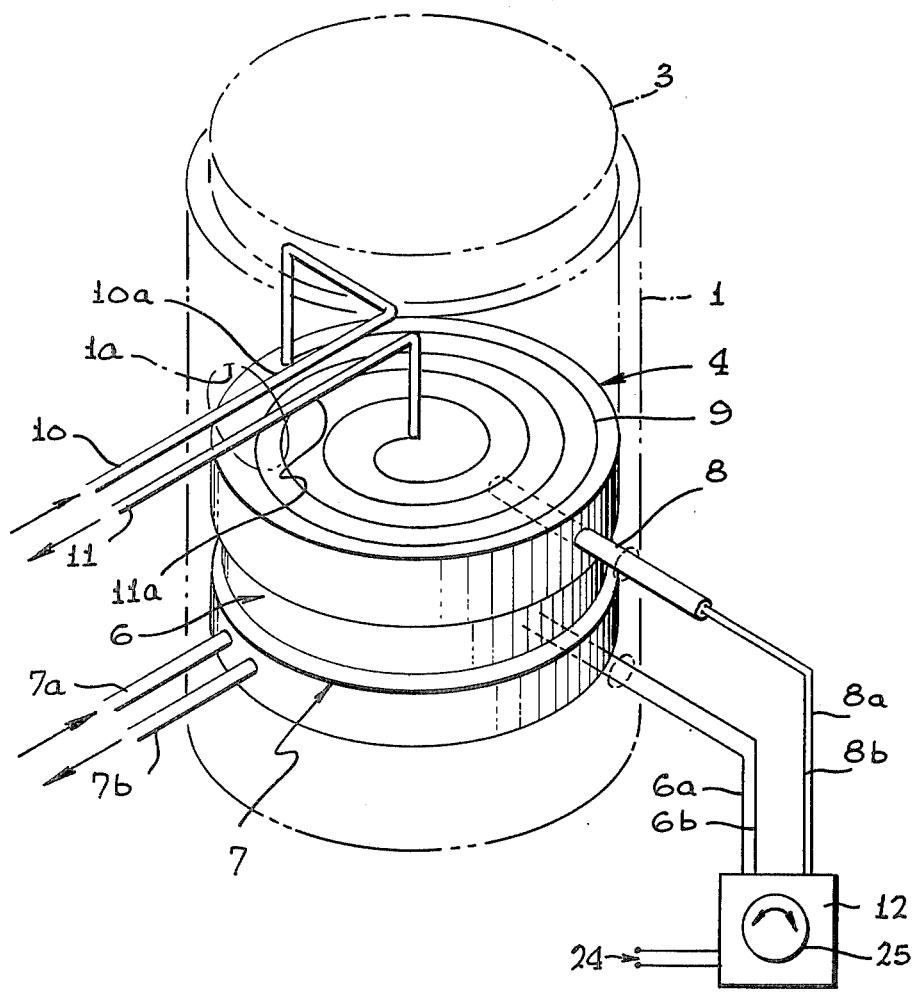
FIG. 2 is a schematic illustration of a thermoelectric device used in the device of FIG. 1.

Turning now to FIG. 2, which schematically illustrates the thermo-electric device used in the apparatus of FIG. 1, there is shown a cylindrical housing 1 which accommodates heat exchangers 4 and 7, and the Peltier element 6. The rinsing liquid to be thermostatically controlled, such as distilled water, is conveyed into the main heat exchanger 4, via the inlet conduit 10, and leaves the heat exchanger 4 through the outlet conduit 11 suitably by means of a pump 22, as described above in connection with FIG. 1. The auxiliary heat exchanger 7 receives the flow of an auxiliary liquid, conducted therethrough by means of inlet conduit 7a and outlet conduit 7b. By well-known means, which need not be described in detail, for example electric heating or electric cooling, the auxiliary liquid, such as water, may be maintained at a temperature with respect to which the Peltier element 6 must transfer only a small quantity of heat for achieving fine adjustment of the temperature of the rinsing liquid.

The Peltier element 6 is disposed between the main heat exchanger 4 and the auxiliary heat exchanger 7 in such a manner that each distinct one of the heat exchangers may be in optimum heat-conductive contact with a different one of the two electrodes which, during operation, perform either as the heat sink of the Peltier element or as the heat source of the Peltier element, depending upon the polarity of the energization current. Thus, the heat exchangers are in direct, large surface contact with the Peltier element. This condition is suitably achieved when both heat exchangers and the Peltier element have a disk-shaped, flat configuration, as shown in FIG. 2.

As is well known, a Peltier element consists of two metallic conductors, frequently and herein referred to as electrodes, between which a temperature gradient is generated when an electrical current is conducted through these conductors and their junction. Therefore, one of the metallic conductors, i.e. electrodes, constitutes a heat sink and the other electrode constitutes a heat source. Reversal of the direction of current results in a reversal between source and sink.

Assuming now that in the illustrated embodiment the rinsing liquid is to be cooled, by way of example, then electric current is conducted via the leads 6a and 6b through the Peltier element 6 in such a manner that the electrode which is in heat-transferring contact with the main heat exchanger 4 becomes the heat sink and the other electrode which is in contact with the auxiliary heat exchanger 7 operates as a heat source. If the auxiliary liquid which is conveyed through the auxiliary heat exchanger 7 is appropriately precooled to a temperature in vicinity of, or almost accurately, the level of the temperature desired for the rinsing liquid, then the temperature change, to be accomplished by the Peltier element to achieve fine adjustment, need only be of small magnitude.

Concentrating now on the temperature control system which regulates the temperature of the rinsing liquid, as it is conveyed through the first, i.e. main heat exchanger 4, the control system includes the temperature sensor 8 which is associated with the heat exchanger 4 such that it penetrates into the depth, so that the internal end of the temperature sensor 8 as is close as possible to the innermost end of the spiraling channel 9 which accommodates the flow of the rinsing liquid in heat exchanger 4, as shown in FIG. 2. The most internal end of the channel 9 is the end which is connected to the outlet connector 11a, and outlet conduit 11.

The output signal from the temperature sensor 8 is applied via lines 8a and 8b to the controller 12, which is schematically indicated in FIG. 2 because controllers are well known circuit components. The controller may be a so-called PID-controller. The controller is provided with an adjusting knob, as illustrated, which permits an operator, such as a doctor or nurse, to set the system so that it will function by regulating the temperature of the rinsing liquid to a desired level within the operating range of the instrument. Also illustrated in FIG. 2 are terminals 24 to which a power supply can be connected so that, whenever the signal from the temperature sensor 8 applied to the controller 12 deviates from the temperature represented by the setting of the knob 25, electrical power will be applied to the Peltier element 6 via lines 6a and 6b, thereby to energize the Peltier element until the signal from the temperature sensor 8 represents a temperature whose level corresponds to that represented by the setting of knob 25, as selected by the operator. Thus, it can be seen that the temperature control circuit operates as a closed-loop servo-system which maintains the control signal substantially at a desired, adjustable level which is that level which represents the desired temperature.

It is well known that Peltier elements operate by transferring heat energy from one electrode, which is then the heat sink, to the other electrode, which thus becomes the heat source. In the illustrated and described embodiment of the invention, the purpose of the auxiliary liquid, as it is conducted through the second heat exchanger 7, is that of maintaining the temperature of the auxiliary heat exchanger 7 at a substantially constant temperature which is in the vicinity of the desired temperature for the rinsing liquid. It is maintained substantially constant by maintaining the liquid conducted through the auxiliary heat exchanger at a constant temperature level. This temperature level, as it is maintained constant by the liquid flowing through it, will then constitute a basis upon which the Peltier element operate, inasmuch as the electrode of the Peltier element which is in the vicinity of the auxiliary heat exchanger 7 can be stated to be clamped to, i.e. maintained at, the constant temperature of the auxiliary heat exchanger. Then it will be substantially the other electrode, which is the electrode in the vicinity of the main heat exchanger 4 which accommodates the flow of the rinsing liquid, whose temperature will be adjusted, if necessary, by the closed-loop servo-system, as described above.

It was found suitable to conduct the rinsing liquid under utilization of a form of counter-current effect through the main heat exchanger 4. In order to implement this, the inlet connector 10a leads to the peripheral rim of the disk-shaped main heat exchanger 4, and there continues into the external end of the heat exchange conduit which has the form of the spiraling channel 9 progressing from outside toward the axis of the main heat exchanger 4, where it is connected to the outlet connector 11a. In the course of flowing through this heat exchange spiral, the rinsing liquid will progressively assume the desired temperature at which time it leaves the device. The liquid conveyed through the auxiliary heat exchanger may also suitably flow through it in a manner which will implement the counter-current principle. It is, therefore, advantageous if the disk-shaped heat exchangers 4 and 7, as well as the disk-shaped Peltier element 6, are mounted coaxially with respect to the common axis of their disks.

Preferably, the spiraling heat exchange conduit 9 is formed by a spiraling groove in the free surface of the main heat exchanger 4, which is the surface facing away from the Peltier element 6. Since, however, the individual turns must be sealed one from the others, a cylindrical closing lid 3, which can be introduced into the housing 1 at the side of the main heat exchanger, is used as a seal, inasmuch as its internal front surface, upon making surface contact with the free surface of the main heat exchanger 4, seals the individual turns of the spiraling groove. Thus, with this modification, FIG. 2 is interpreted to constitute an exploded view, showing the lid 3 at a distance from its actual position. When it will be lowered to form the seal, the lowermost ends of the vertical lengths of the inlet and outlet connectors 10a and 11a, respectively, will pass through bores (not shown) in the lid 3. Alternatively, the bores may constitute the inlet and outlet connectors for the conduits for the rinsing liquid. Thus, the connectors 10a and 11a, forming the inlet and the outlet for the rinsing liquid, may be machined into the lid 3, so that, upon proper insertion of the lid, the connection between the heat exchange conduit 9 and the mentioned connectors will be accomplished automatically. Insertion of the closing lid 3 at the proper angle into the housing can be implemented by suitable guide elements, such as the use of a protrusion on the lid 3 slidably engaged in an axial groove (not shown) of the housing, for example. The lid 3 should tightly fit into the housing 1 in order to constitute an at least liquid-tight seal, so that the rinsing liquid to be thermostatically controlled cannot, even partly, escape when it flows through the heat exchanger 4.

The heat exchange conduit can also be formed by a hose (not shown) preferably made from plastics or synthetic rubber, which is inserted into the spiraling groove 9 in the free surface of the main heating exchanger 4. As a result, direct liquid contact with the heat exchanger is limited to occur only at the two locations of the connectors and a rather undisturbed flow of rinsing liquid is obtained, which is particularly advantageous in connection with the above-described diagnostic measuring methods.

In connection with the illustrated embodiment, in order to achieve satisfactory connection of the conduits 10 and 11 forming the inlet and outlet for the rinsing liquid with the connectors 10a and 11a within the closing lid 3, a separate coupling element in the form of a plug (not shown) can be provided which can be inserted through an appropriate opening in the housing into a recess within the lid, so that the channels of the connectors 10a and 11a continue into the heat exchanger spiraling channel 9.

The thermostatic control system thus described, when associated with the disclosed medical diagnostic device, has the particular advantage, which is specifically useful in connection with such medical applications, that it is small and of low weight, and that it permits accurate temperature control of even very small quantities of flowing liquid.

We claim:

1. A medical diagnostic device for determining bleeding times and behavior of bleedings from a standardized wound, comprising
    means for establishing a flow of a rinsing liquid past the wound thereby to contact the wound;
    means for determining a characteristic of the rinsing liquid which is representative of the blood contents in the rinsing liquid having contacted the wound; and
    means for controlling the temperature of the rinsing liquid; wherein the temperature control means comprise a first heat exchanger for receiving the flow of the rinsing liquid therethrough, a second heat exchanger for receiving the flow of a second, auxiliary liquid therethrough, a temperature control element in thermal contact with the first and second heat exchangers, and means for controlling energization of the Peltier element as a function of the temperature of the rinsing liquid.

2. Device according to claim 1, wherein the temperature control element comprises a Peltier element.

3. Device according to claim 2, wherein the flow-establishing means comprise a reservior for the rinsing liquid, a flow-through cuvette, a pump for the rinsing liquid and a plurality of conduits for serially interconnecting the reservoir, the temperature control means, the flow-through cuvette, the pump and the means for determining a characteristic of the rinsing liquid.

4. Device according to claim 1, wherein the means for determining a characteristic of the rinsing liquid comprise a photometric instrument including a light-transmissive container, a light source, a photocell for receiving light emitted from the light source and passing through the container, and means for monitoring the output from the photocell.

5. Device according to claim 2, wherein the means for controlling energization of the Peltier element comprise a servo-system including the temperature sensing means associated with the first heat exchanger and also including control means for energizing the Peltier element, the servo-system being operable to maintain the temperature of the first liquid substantially at a predetermined level.

6. Device according to claim 2, the energization control means comprising a temperature sensor associated with the first heat exchanger for generating a control signal which is representative of the temperature of the rinsing liquid, a power source for energizing the Peltier element, and a controller for receiving the control signal and regulating the power applied to the Peliter element in a closed-loop servo-system in such a manner that the controlsignal is maintained substantially at a desired adjustable level.

7. Device according to claim 2, wherein the temperature of the auxiliary liquid is substantially constant and in vicinity of a desired temperature for the rinsing liquid represented by the desired level of the control signal.

8. Device according to claim 7, wherein the Peltier element electrode adjacent to the second heat exchanger is maintained at a substantially constant temperature by virtue of the flow of the liquid through the second heat exchanger.

9. Device according to claim 2, wherein each of the heat exchangers and the Peltier element are of flat, disk-shaped configuration and coaxially assembled, with the Peltier element mounted between the heat exchangers.

10. Device according to claim 9, wherein at least one of the heat exchangers has a spiraling groove formed in its surface facing away from the Peltier element and a lid is sealingly secured to the grooved surface, the groove thus forming a spiraling channel.

* * * * *